US007282197B2

(12) United States Patent  (10) Patent No.: US 7,282,197 B2
Diec et al.  (45) Date of Patent: *Oct. 16, 2007

(54) ANTIPERSPIRANT GEL

(75) Inventors: Khiet Hien Diec, Hamburg (DE); Ulrich Kux, Hamburg (DE)

(73) Assignee: Beiersdorf AG, Hamburg (DE)

( * ) Notice: Subject to any disclaimer, the term of this patent is extended or adjusted under 35 U.S.C. 154(b) by 553 days.

This patent is subject to a terminal disclaimer.

(21) Appl. No.: 10/892,159

(22) Filed: Jul. 16, 2004

(65) Prior Publication Data
US 2005/0048013 A1   Mar. 3, 2005

(30) Foreign Application Priority Data
Jul. 19, 2003 (DE) .................. 103 32 928

(51) Int. Cl.
*A61Q 15/00*  (2006.01)
*A61K 8/02*  (2006.01)
*A61K 8/06*  (2006.01)

(52) U.S. Cl. .................. 424/65; 424/66; 424/68; 424/400; 424/401; 514/937; 514/938; 514/939

(58) Field of Classification Search .................. 424/65, 424/400, 401, 66, 68; 514/937, 938, 939
See application file for complete search history.

(56) References Cited

U.S. PATENT DOCUMENTS

| | | | |
|---|---|---|---|
| 4,788,001 A | 11/1988 | Narula | |
| 4,921,694 A | 5/1990 | Hoppe et al. | |
| 5,077,040 A | 12/1991 | Bergmann et al. | |
| 5,318,778 A | 6/1994 | Schmucker et al. | |
| 5,487,887 A | 1/1996 | Benfatto | |
| 5,500,209 A | 3/1996 | Ross et al. | |
| 5,534,246 A | 7/1996 | Herb et al. | |
| 5,648,067 A | 7/1997 | Dillenburg et al. | |
| 5,718,888 A | 2/1998 | Klier et al. | |
| 5,734,029 A | 3/1998 | Wulff et al. | |
| 6,033,651 A | 3/2000 | Dolak et al. | |
| 6,171,581 B1 | 1/2001 | Joshi et al. | |
| 6,498,197 B1 | 12/2002 | Bialek et al. | |
| 6,607,733 B1 | 8/2003 | Diec et al. | |
| 6,667,044 B1 | 12/2003 | Diec et al. | |
| 6,749,841 B2 | 6/2004 | Joshi et al. | |
| 2003/0031638 A1 | 2/2003 | Joshi et al. | |
| 2003/0059385 A1 | 3/2003 | Ansmann et al. | |

FOREIGN PATENT DOCUMENTS

| | | |
|---|---|---|
| DE | 3740186 | 1/1989 |
| DE | 3938140 | 8/1991 |
| DE | 4009347 | 9/1991 |
| DE | 4204321 | 8/1993 |
| DE | 4229707 | 3/1994 |
| DE | 4229737 | 3/1994 |
| DE | 4237081 | 5/1994 |
| DE | 4309372 | 9/1994 |
| DE | 4324219 | 1/1995 |
| DE | 10164470 | 7/2003 |
| EP | 1027880 | 8/2000 |
| WO | 92/05767 | 4/1992 |
| WO | 95/12379 | 5/1995 |
| WO | 96/23483 | 8/1996 |
| WO | 92/28132 | 9/1996 |
| WO | 98/15254 | 4/1998 |
| WO | 01/47474 | 7/2001 |
| WO | 02/49591 | 6/2002 |
| WO | 03/009819 | 2/2003 |
| WO | 03/030852 | 4/2003 |
| WO | 03/053396 | 7/2003 |
| WO | 03/082182 | 10/2003 |

OTHER PUBLICATIONS

English Language Abstract of DE 10164470.
English Language Abstract of DE 4009347.
English Language Abstract of DE 4204321.
English Language Abstract of DE 4229707.
English Language Abstract of DE 4229737.
English Language Abstract of DE 4324219.
Goldschmidt informiert 1982, 57, pp. 22-28 "Herstellung von Mikroemulsionsgelen with TEGO®- Tensiden" (Preparation of Microemulsion Gels with TEGO® Surfactants).
Happi, Feb. 1993, pp. 58, 60, 62 and 64, "Microemulsion Gels: A Formulators Guide".

*Primary Examiner*—Shelley A. Dodson
(74) *Attorney, Agent, or Firm*—Greenblum & Bernstein, P.L.C.

(57) ABSTRACT

A cosmetic or dermatological composition for preventing excessive odor and sweat secretion by skin, comprising an optically translucent to transparent, substantially alcohol-free oil-in-water type emulsion gel which comprises a polyethoxylated and/or a polypropoxylated O/W emulsifier, a polyol and a antiperspirant. This abstract is neither intended to define the invention disclosed in this specification nor intended to limit the scope of the invention in any way.

48 Claims, No Drawings

ANTIPERSPIRANT GEL

CROSS-REFERENCE TO RELATED APPLICATIONS

The present application claims priority under 35 U.S.C. §119 of German Patent Application No. 103 32 928.5 filed on Jul. 19, 2003, the disclosure of which is expressly incorporated by reference herein in its entirety.

BACKGROUND OF THE INVENTION

1. Field of the Invention

The present invention relates to an optically translucent to transparent antiperspirant formulation of an oil-in-water emulsion gel, in particular of an oil-in-water microemulsion gel, and has a viscosity of at least 5,000 mPa s with a high content of antiperspirant salt.

2. Discussion of Background Information

The human skin is covered with two to three million sweat glands. These are used day and night to convey moisture to the surface of the skin and thus to prevent the organism from overheating. The sweat which emerges ensures the necessary cooling as it evaporates.

In the normal case, 0.5 to 1 litre of sweat are produced daily. In cases of strain on the body and increased metabolism, it may be many times the amount of produced sweat. The course of the development of a human involves the formation of two types of sweat glands. From birth onwards, a person has only ecrine sweat glands (small sweat glands) but the onset of puberty sees the formation of the apocrine sweat glands (large sweat glands), primarily in the area of the armpits and in the anal and genital regions. Only the latter, in combination with skin bacteria which decompose the odorless sweat, lead to the known unpleasant odors. The odor of sweat is person-specific and is pronounced to different degrees for each person. For most people, simple washing can only achieve a short-term improvement, meaning that often enough it is not possible without the use of deodorant active ingredients. In order to achieve a deodorant effect, there are various ways which, in the normal case, are used in combination.

The use of antiperspirants which prevent the production of sweat by blocking the openings of sweat glands has been known for a long time. Use is usually made here of aluminium and aluminium/zirconium salts. According to the latest findings, the reduced sweat production has no effect on the organism since the "cooling effect" largely takes place via the "sweating" of the other areas of the skin (ecrine glands).

The inhibition of bacterial growth as a result of bacteriostats in the area of the skin zones covered with apocrine sweat glands is not acceptable and sometimes leads to severe irritations and allergic reactions.

The alcohol (ethanol) which is present in many of the conventional deodorant products also acts as bactericide. Here too, side-effects are often common.

To mask the odor of sweat, fragrances or perfume substances are usually present in the deodorant preparations. Some of these also have a bacteriostatic effect, but with many of them users have similar side-effects as the bacteriostats.

Due to the mode of action described above and the side-effects associated therewith, the attempts to develop deodorant products which do not have side-effects are numerous. The trend is thus clearly in the direction of a combination product in which a deodorizing and antiperspirant effect accompanies a skincare effect.

Such care deodorants based on O/W emulsions have already entered the market, but handling, that is to say application to the skin, still leaves a lot to be desired.

Transparent and translucent products are preferred by many consumers primarily for aesthetic reasons. The combination of this feature with the wish for highly effective antiperspirant products has hitherto only been realized with aqueous-alcoholic formulations. These formulations consist virtually only of water and alcohol as medium, deodorant and antiperspirant agents as active ingredients, and perfume, solubility promoters and thickeners (in most cases based on carbohydrate) as additional agents. They are perceived by the consumer as being fresh and cooling, but are at the same time burdened with a whole series of shortcomings. For example, the application primarily to freshly shaved skin is associated with incompatibilities as a result of the alcohol content. A further significant disadvantage is the fact that relatively large amounts of oil cannot be incorporated into such systems. As a result of the high content of antiperspirant salt required for a highly effective performance, a white residue remains on the skin following application, which is perceived as highly undesirable by the consumer. As a result of the absence, brought about technologically, of a sufficiently large oil phase however, this cannot be concealed. Moreover, the use of carbohydrate thickeners leads to a certain stickiness of the product after the alcohol has evaporated. In summary, it may be said that aqueous-alcoholic formulations are not suitable as a base for the incorporation of high contents of antiperspirant agents (aluminium or aluminium/zirconium complexes).

The solution to all of these disadvantages has been a long time coming. Only recently have also cosmetically pleasing alcohol-free-transparent products been possible which are based on so-called microemulsions. These have the great advantage that even relatively large amounts of various oils—with all of the above-described positive effects for the consumer—can be stably incorporated. Formulations of this type are in principle obtainable by means of phase-inversion temperature technology (PIT) or high-pressure homogenization. The necessary stability of the emulsifier system to high concentrations of antiperspirant salts, however, places high requirements on the formulating skill of the product developer. In order to achieve transparency, the refractive indices of the oil phase and of the water phase must be virtually identical. Even a deviation above 0.0004 leads to clouding of the formulation. The preparation of transparent formulations is described in WO92/05767.

Besides the water-in-silicon emulsion gels, anhydrous oleogels and hydrogels based on carbomers are also available commercially.

For the application of antiperspirants, many consumers favour the product form of the so-called roll-on or deodorant sticks, since these allow the contents to be applied to the armpit region in finely distributed form without the fingers having to be brought into contact therewith. Compared with aerosols, there is also the ecological advantage that a roll-on and a deodorant stick do not use propellants (liquefied gases).

SUMMARY OF THE INVENTION

The present invention comprises a cosmetic and/or dermatological composition for preventing excessive odor and sweat secretion by the skin. This composition comprises an optically translucent to transparent, substantially alcohol-free oil-in-water (O/W) type emulsion gel which comprises, based on the total weight of the emulsion,
   a. not more than about 20% by weight of one or more O/W emulsifiers selected from polyethoxylated O/W emulsifiers, polypropoxylated O/W emulsifiers and combinations thereof and, of one or more optional W/O emulsifiers,
   b. from about 1% to about 30% by weight of at least one polyol,
   c. from about 5% to about 40% by weight of at least one antiperspirant.

In one aspect, the composition may be obtainable by mixing and heating the components thereof until they have substantially dissolved, and then cooling to room temperature with stirring.

In another aspect, the emulsion may comprise a microemulsion. In yet another aspect, the emulsion may comprise a discontinuous phase comprising droplets which may be joined together by the at least one polyol. For example, the droplets may have an average size of less than about 100 nm.

In a still further aspect, the composition may have a viscosity of at least about 5,000 mPa s, e.g., at least about 10,000 mPa s, and/or the composition may have a viscosity of not higher than about 500,000 mPa s, e.g., not higher than about 400,000 mpa.s, or not higher than about 300,000 mPa.s. For example, the composition may be a thick (viscous) liquid or a semi-solid.

In another aspect of the composition of the present invention, the at least one antiperspirant may comprise at least one acidic salt such as, e.g., a salt which comprises aluminium and/or zirconium. For example, the antiperspirant may comprise an aluminum salt and/or an aluminum/zirconium salt in a total amount of at least about 5% by weight, based on the total weight of the composition.

In yet another aspect, the composition may comprise from about 10% to about 30% by weight of antiperspirant(s), based on the total weight of the composition.

In another aspect, the composition may comprise from about 0.1% to about 20% by weight, e.g., from about 0.5% to about 18% by weight, or from about 1% to about 14% by weight of the polyethoxylated O/W emulsifier(s) and/or of the polypropoxylated O/M emulsifier(s), based on the total weight of the composition.

In yet another aspect, the composition may comprise from about 0.1% to about 5% by weight, e.g., from about 0.5% to about 3.5% by weight, or from about 1% to about 2.5% by weight of the W/O emulsifier(s), based on the total weight of the composition.

In a still further aspect, the composition may comprise from about 8% to about 20% by weight of the polyol(s). By way of non-limiting example, the polyol(s) may comprise one or more of glycerol, propylene glycol, dipropylene glycol, sorbitol, and butylene glycol. For example, the composition may comprise glycerol, either alone or in combination with one or more of propylene glycol, dipropylene glycol, sorbitol, and butylene glycol.

In another aspect, the composition may comprise, based on the total weight of the composition, from about 1% to about 14% by weight of the one or more polyethoxylated O/W emulsifiers and/or from about 1% to about 14% by weight of the one or more polypropoxylated O/W emulsifiers, and from about 8% to about 20% by weight of the at least one polyol, in particular, glycerol. This composition may further comprise from about 1% to about 2.5% by weight of the one or more W/O emulsifiers and/or from about 10% to about 30% by weight of the at least one antiperspirant, e.g., an acidic aluminum salt and/or an acidic aluminum/zirconium salt in a total amount of at least about 5% by weight.

In a still further aspect of the composition of the present invention, the composition may further comprise an active ingredient and/or a perfume and/or a fragrance.

The present invention also provides a process for making the composition of the present invention, including the various aspects thereof. This process comprises heating a mixture of the components thereof until the components have substantially or completely dissolved and thereafter cooling the mixture to room temperature with stirring. In one aspect, this process will not include a homogenization operation.

The present invention also provides a cosmetic stick, a deodorant roll-on container and an atomizer pump container, all of which comprise the composition of the present invention, including the various aspects thereof.

The present invention also provides a method of reducing the secretion of sweat by the (human) skin and/or of reducing excessive odor generated by the skin. This method comprises the application to at least parts of the skin (e.g., the armpit area and/or the genital region) the composition of the present invention, including the various aspects thereof.

Surprisingly, the formulations which may advantageously be used for ameliorating the above-described problems are optically translucent to transparent, substantially alcohol-free emulsion gels, based on emulsions of the oil-in-water type, in particular microemulsion gels of the oil-in-water type, which comprise an oil phase and a water phase comprising:
   one or more O/w emulsifiers and/or one or more crosslinkers, in particular polyols,
   optionally, also comprising one or more W/O emulsifiers,
   an emulsifier content of not more than about 20% by weight, based on the total weight of the emulsion,
   an antiperspirant content of from about 5% to about 40% by weight, based on the total weight of the emulsion,
   a polyol content of about 1% to about 30% by weight, based on the total weight of the emulsion, obtainable, for example, by bringing a mixture of the basic components, comprising water phase, oil phase, O/W emulsifiers according to the invention, if desired W/O emulsifiers, and if desired further auxiliaries, additives and/or active ingredients, to a temperature at which all of the components are substantially dissolved and subsequently cooling it to room temperature with stirring, without homogenizing the emulsion and in which the droplets of the discontinuous oil phase may be joined together by polyols.

Transparent gels according to the invention have a low viscosity, are especially suitable as vehicles for a very wide variety of active ingredients, in particular lipid-soluble active ingredients and, moreover, are characterized by excellent skin and mucosa compatibility.

The crosslinker substances used in the invention are the polyols, in particular the triols, which form an independent gel network and effect cohesion of the network with the emulsion droplets at the points of intersection of the network.

All of the constituents—apart from water and fragrances—of the emulsion gels according to the invention generally are of low volatility, i.e., in the pure state they have a low vapor pressure at 25° C., as a result of which drying off and crystal formation is suppressed.

It is advantageous for the purposes of the invention when the oil-in-water emulsion appears optically translucent to transparent and has a particle size of less than about 100 nm. Emulsions with average particle sizes below about 100 nm are generally referred to as microemulsions The one or more O/M emulsifiers may advantageously include one or more of the following:

fatty alcohol ethoxylates of the general formula R—O—(—CH$_2$—CH$_2$—O—)$_n$—H, where R is a branched or unbranched alkyl, aryl or alkenyl radical and n is a number of from about 10 to about 50, ethoxylated wool wax alcohols, polyethylene glycol ethers of the general formula R—O—(—CH$_2$—CH$_2$—O—)$_n$—R', where R and R', independently of one another, are branched or unbranched alkyl or alkenyl radicals and n is a number of from about 10 to about 80, fatty acid ethoxylates of the general formula R—COO—(—CH$_2$—CH$_2$—O—)$_n$—H, where R is a branched or unbranched alkyl or alkenyl radical and n is a number of from about 10 to about 40, etherified fatty acid ethoxylates of the general formula R—COO—(—CH$_2$—CH$_2$—O—)$_n$—R', where R and R', independently of one another, are branched or unbranched alkyl or alkenyl radicals and n is a number of from about 10 to about 80, esterified fatty acid ethoxylates of the general formula R—COO—(—CH$_2$—CH$_2$—O—)$_n$—C(O)—R', where R and R', independently of one another, are branched or unbranched alkyl or alkenyl radicals and n is a number of from about 10 to about 80, polyethylene glycol glycerol fatty acid esters of saturated and/or unsaturated, branched and/or unbranched fatty acids having a degree of ethoxylation of form about 3 to about 50, ethoxylated sorbitan esters with a degree of ethoxylation of from about 3 to about 100, cholesterol ethoxylates with a degree of ethoxylation of from about 3 to about 50, ethoxylated triglycerides with a degree of ethoxylation of form about 3 to about 150, alkyl ether carboxylic acids of the general formula R—O—(—CH$_2$—CH$_2$—O—)$_n$—CH$_2$—COOH or cosmetically or pharmaceutically acceptable salts thereof, where R is a branched or unbranched alkyl or alkenyl radical having from about 5 to about 30 carbon atoms and n is a number from about 5 to about 30, polyoxyethylene sorbitol fatty acid esters based on branched or unbranched alkanoic or alkenoic acids and having a degree of ethoxylation of from about 5 to about 100, for example of the sorbeth type, alkyl ether sulphates or the acids on which the sulphates are based of the general formula R—O—(—CH$_2$—CH$_2$—O—)$_n$—SO$_3$-H with cosmetically or pharmaceutically acceptable cations, where R is a branched or unbranched alkyl or alkenyl radical having from about 5 to about 30 carbon atoms and n is a number of from about 1 to about 50, fatty alcohol propoxylates of the general formula R—O—(—CH$_2$—CH(CH$_3$)—O—)$_n$—H, where R is a branched or unbranched alkyl or alkenyl radical and n is a number of from about 10 to about 80, polypropylene glycol ethers of the general formula R—O—(—CH$_2$—CH(CH$_3$)—O—)$_n$—R', where R and R', independently of one another, are branched or unbranched alkyl or alkenyl radicals and n is a number of from about 10 to about 80, propoxylated wool wax alcohols, etherified fatty acid propoxylates of the general formula R—COO—(—CH$_2$—CH(CH$_3$)—O—)$_n$—R', where R and R', independently of one another, are branched or unbranched alkyl or alkenyl radicals and n is a number of from about 10 to about 80, esterified fatty acid propoxylates of the general formula R—COO—(—CH$_2$—CH(CH$_3$)—O—)$_n$—C(O)—R', where R and R', independently of one another, are branched or unbranched alkyl or alkenyl radicals and n is a number of from about 10 to about 80, fatty acid propoxylates of the general formula R—COO—(—CH$_2$—CH(CH$_3$)—O—)$_n$—H, where R is a branched or unbranched alkyl or alkenyl radical and n is a number of from about 10 to about 80, polypropylene glycol glycerol fatty acid esters of saturated and/or unsaturated, branched and/or unbranched fatty acids having a degree of propoxylation of from about 3 to about 80, propoxylated sorbitan esters with a degree of propoxylation of from about 3 to about 100, cholesterol propoxylates with a degree of propoxylation of from about 3 to about 100, propoxylated triglycerides with a degree of propoxylation of from about 3 to about 100, alkyl ether carboxylic acids of the general formula R—O—(—CH$_2$—CH(CH$_3$)O—)$_n$—CH$_2$—COOH or cosmetically or pharmaceutically acceptable salts thereof, where R is a branched or unbranched alkyl or alkenyl radical and n is a number of from about 3 to about 50, alkyl ether sulphates and/or the acids on which the sulphates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having from about 5 to about 30 carbon atoms and n is a number of from about 1 to about 50, fatty alcohol ethoxylates/propoxylates of the general formula R—O—X$_n$—Y$_m$—H, where R is a branched or unbranched alkyl or alkenyl radical, X and Y are not identical and are in each case either an oxyethylene group or an oxypropylene group and n and m, independently of one another, are numbers of from about 5 to about 50, polypropylene glycol ethers of the general formula R—O—X$_n$—Y$_m$—R', where R and R', independently of one another, are branched or unbranched alkyl or alkenyl radicals, where X and Y are not identical and are in each case either an oxyethylene group or an oxypropylene group and n and m, independently of one another, are numbers of from about 5 to about 100, etherified fatty acid propoxylates of the general formula R—COO—X$_n$—Y$_m$—R', where R and R', independently of one another, are branched or unbranched alkyl or alkenyl radicals, where X and Y are not identical and are in each case either an oxyethylene group or an oxypropylene group and n and m, independently of one another, are numbers of from about 5 to about 100, fatty acid ethoxylates/propoxylates of the general formula R—COO—X$_n$—Y$_m$—H, where R is a branched or unbranched alkyl or alkenyl radical, where X and Y are not identical and are in each case either an oxyethylene group or an oxypropylene group and n and m, independently of one another, are numbers of from about 5 to about 50.

It is particularly advantageous if the one or more polyethoxylated or polypropoxylated and/or polyethoxylated and polypropoxylated O/W emulsifiers comprise one or more of the following:

fatty alcohol ethoxylates of the general formula R—O—(—CH$_2$—CH$_2$—O—)$_n$—H, where R is a branched or unbranched alkyl or alkenyl radical having from about 5 to about 30 carbon atoms and n is a number of from about 10 to about 25, ethoxylated wool wax alcohols with HLB values of from about 8 to about 17, very particularly advantageously with HLB values of from about 12 to about 16, polyethylene glycol ethers of the general formula R—O—(—CH$_2$—CH$_2$—O—)$_n$—R', where R and R', independently of one another, are branched or unbranched alkyl or alkenyl radicals having from about 5 to about 30 carbon atoms and n is a number of from about 10 to about 25, fatty acid ethoxylates of the general formula R—COO—(—CH$_2$—CH$_2$—O—)$_n$—H, where R is a branched or unbranched alkyl or alkenyl radical having from about 5 to about 30 carbon atoms and n is a number of from about 10 to about 25, etherified fatty acid ethoxylates of the general formula R—COO—(—CH$_2$—CH$_2$—O—)$_n$—R', where R and R', independently of one another, are branched or unbranched alkyl or alkenyl radicals having from about 5 to about 30 carbon atoms and n is a number of from about 10 to about 50, esterified fatty acid ethoxylates of the general formula R—COO—(—CH$_2$—CH$_2$—O—)$_n$—C(O)—R', where R and R', independently of one another, are branched or unbranched alkyl or alkenyl radicals having from about 5 to about 30 carbon atoms and n is a number of from about 10 to about 50, polyethylene glycol glycerol fatty acid esters of saturated and/or unsaturated, branched and/or unbranched fatty acids having from about 6 to about 26 carbon atoms and a degree of ethoxylation of from about 3 to about 40, ethoxylated sorbitan esters with a degree of ethoxylation of from about 3 to about 30, cholesterol ethoxylates with HLB values of from about 8 to about 17, very particularly advantageously with HLB values of from about 12 to about 16, ethoxylated triglycerides with HLB values of from about 8 to about 17, very particularly advantageously with HLB values of from about 12 to about 16, alkyl ether carboxylic acids of the general formula R—O—(—CH$_2$—CH$_2$—O—)$_n$—CH$_2$—COOH or cosmetically or pharmaceutically acceptable salts thereof, where R is a branched or unbranched alkyl or alkenyl radical having from about 5 to about 30 carbon atoms and n is a number of from about 10 to about 20, polyoxyethylene sorbitol fatty acid esters based on branched or unbranched alkanoic or alkenoic acids and having a degree of ethoxylation of from about 10 to about 80, for example of the sorbeth type, alkyl ether sulphates and/or acids on which the sulphates are based of the general formula R—O—(—CH$_2$—CH$_2$—O—)$_n$—SO$_3$—H with cosmetically or pharmaceutically acceptable cations, where R is a branched or unbranched alkyl or alkenyl radical having from about 5 to about 30 carbon atoms and n is a number of from about 3 to about 30, fatty alcohol propoxylates of the general formula R—O—(—CH$_2$—CH(CH$_3$)—O—)$_n$—H, where R is a branched or unbranched alkyl or alkenyl radical having from about 5 to about 30 carbon atoms and n is a number of from about 10 to about 30, polypropylene glycol ethers of the general formula R—O—(—CH$_2$—CH(CH$_3$)—O—)$_n$—R', where R and R', independently of one another, are branched or unbranched alkyl or alkenyl radicals having from about 5 to about 30 carbon atoms and n is a number of from about 10 to about 40, propoxylated wool wax alcohols with HLB values of from about 8 to about 17, very particularly advantageously with HLB values of from about 12 to about 16, fatty acid propoxylates of the general formula R—COO—(—CH$_2$—CH(CH$_3$)—O—)$_n$—H, where R is a branched or unbranched alkyl or alkenyl radical having from about 5 to about 30 carbon atoms and n is a number of from about 10 to about 40, etherified fatty acid propoxylates of the general formula R—COO—(—CH$_2$—CH(CH$_3$)—O—)$_n$—R', where R and R', independently of one another, are branched or unbranched alkyl or alkenyl radicals having from about 5 to about 30 carbon atoms and n is a number of from about 10 to about 30, esterified fatty acid propoxylates of the general formula R—COO—(—CH$_2$—CH(CH$_3$)—O—)$_n$—C(O)—R', where R and R', independently of one another, are branched or unbranched alkyl or alkenyl radicals having from about 5 to about 30 carbon atoms and n is a number of from about 10 to about 50, polypropylene glycol glycerol fatty acid esters of saturated and/or unsaturated, branched and/or unbranched fatty acids having from about 6 to about 26 carbon atoms and a degree of propoxylation of from about 3 to about 50, propoxylated sorbitan esters with a degree of propoxylation of from about 3 to about 80, cholesterol propoxylates with HLB values of from about 8 to about 17, very particularly advantageously with HLB values of from about 12 to about 16, propoxylated triglycerides with HLB values of from about 8 to about 17, very particularly advantageously with HLB values of from about 12 to about 16, alkyl ether carboxylic acids of the general formula R—O—(—CH$_2$—CH(CH$_3$)O—)$_n$—CH$_2$—COOH or cosmetically or pharmaceutically acceptable salts thereof, where R is a branched or unbranched alkyl or alkenyl radical having from about 5 to about 30 carbon atoms and n is a number of from about 10 to about 30, alkyl ether sulphates and/or the acids on which the sulphates are based of the general formula R—O—(—CH$_2$—CH(CH$_3$)—O—)$_n$—SO$_3$—H with cosmetically or pharmaceutically acceptable cations, where R is a branched or unbranched alkyl or alkenyl radical having from about 5 to about 30 carbon atoms and n is a number of from about 1 to about 30.

According to the invention, the polyethoxylated or polypropoxylated and/or the polyethoxylated and polypropoxylated O/W emulsifiers are particularly advantageously selected from substances with HLB values of from about 8 to about 17, very particularly advantageously with HLB values of from about 12 to about 16 if the O/W emulsifiers have saturated radicals R and R'. If the O/W emulsifiers have unsaturated radicals R and/or R', or if isoalkyl derivatives are present, then the preferred HLB value of such emulsifiers may also be lower or higher.

It is advantageous to select the fatty alcohol ethoxylates from one or more of ethoxylated octyldodecyl alcohols, stearyl alcohols, cetyl alcohols, cetylstearyl alcohols (cetearyl alcohols), behenyl alcohols. Particular preference is given to:

polyethylene glycol(16) octyldodecyl ether (octyldodeceth-16), polyethylene glycol(20) octyldodecyl ether (octyldodeceth-20), polyethylene glycol(25) octyldodecyl ether (octyldodeceth-25), polyethylene glycol(13) stearyl ether (steareth-13), polyethylene glycol-(14) stearyl ether (steareth-14), polyethylene glycol(15) stearyl ether (steareth-15), polyethylene glycol(16) stearyl ether (steareth-16), polyethylene glycol (17) stearyl ether (steareth-17), polyethylene glycol(18) stearyl ether (steareth-18), polyethylene glycol(19) stearyl ether (steareth-19), polyethylene glycol (20) stearyl ether (steareth-20);

polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20);

polyethylene glycol(13) cetyl ether (ceteth-13), polyethylene glycol(14) cetyl ether (ceteth-14), polyethylene glycol (15) cetyl ether (ceteth-15), polyethylene glycol(16) cetyl ether (ceteth-16), polyethylene glycol(17) cetyl ether (ceteth-17), polyethylene glycol(18) cetyl ether (ceteth-18), polyethylene glycol(19) cetyl ether (ceteth-19), polyethylene glycol(20) cetyl ether (ceteth-20);

polyethylene glycol(13) isocetyl ether (isoceteth-13), polyethylene glycol(14) isocetyl ether (isoceteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol (18) isocetyl ether (isoceteth-18), polyethylene glycol(19) isocetyl ether (isoceteth-19), polyethylene glycol(20) isocetyl ether (isoceteth-20);

polyethylene glycol(12) oleyl ether (oleth-12), polyethylene glycol(13) oleyl ether (oleth-13), polyethylene glycol (14) oleyl ether (oleth-14), polyethylene glycol(15) oleyl ether (oleth-15);

polyethylene glycol(12) lauryl ether (laureth-12), polyethylene glycol(12) isolauryl ether (isolaureth-12);

polyethylene glycol(13) cetylstearyl ether (ceteareth-13), polyethylene glycol(14) cetyl stearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), polyethylene glycol(20) cetylstearyl ether (ceteareth-20), polyethylene glycol(10) behenyl ether (beheneth-10), polyethylene glycol(20) behenyl ether (beheneth-20), polyethylene glycol(25) behenyl ether (beheneth-25), and polyethylene glycol(30) behenyl ether (beheneth-30).

It is also advantageous to select the fatty acid ethoxylates from one or more of the following ethoxylates:

polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol (13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol (21) isostearate, polyethylene glycol(22) isostearate, polyethylene glycol(23) isostearate, polyethylene glycol(24) isostearate, polyethylene glycol(25) isostearate, polyethylene glycol(12) oleate, polyethylene glycol(13) oleate, polyethylene glycol(14) oleate, polyethylene glycol (15) oleate, polyethylene glycol(16) oleate, polyethylene glycol(17) oleate, polyethylene glycol(18) oleate, polyethylene glycol(19) oleate, polyethylene glycol(20) oleate.

A preferred example of an ethoxylated alkyl ether carboxylic acid or salt thereof which may be used particularly advantageously is sodium laureth-11 carboxylate.

Sodium laureth-14 sulphate may particularly advantageously be used as alkyl ether sulphate.

A preferred example of an ethoxylated cholesterol derivative which may be used particularly advantageously is polyethylene glycol(30) cholesterol ether. Polyethylene glycol(25) soyasterol may also be particularly useful.

Preferred examples of ethoxylated triglycerides which may be used particularly advantageously include polyethylene glycol(60) evening primrose glycerides.

It may also be advantageous to select the polyethylene glycol glycerol fatty acid esters from one or more of polyethylene glycol(20) glyceryl laurate, polyethylene glycol(21) glyceryl laurate, polyethylene glycol(22) glyceryl laurate, polyethylene glycol(23) glyceryl laurate, polyethylene glycol(6) glyceryl caprate, polyethylene glycol(20) glyceryl oleate, polyethylene glycol(20) glyceryl isostearate, and polyethylene glycol(18) glyceryl oleate/cocoate.

It may likewise be favorable to select the sorbitan esters from one or more of polyethylene glycol(20) sorbitan monolaurate, polyethylene glycol(20) sorbitan monostearate, polyethylene glycol(20) sorbitan monoisostearate, polyethylene glycol(20) sorbitan monopalmitate, and polyethylene glycol(20) sorbitan monooleate.

Advantageous examples of the optionally employed W/O emulsifiers include: fatty alcohols having from about 8 to about 30 carbon atoms, monoglycerol esters of saturated and/or unsaturated, branched and/or unbranched alkanecarboxylic acids with a chain length of from about 8 to about 24, in particular of from about 12 to about 18, carbon atoms, diglycerol esters of saturated and/or unsaturated, branched and/or unbranched alkanecarboxylic acids with a chain length of from about 8 to about 24, in particular from about 12 to about 18, carbon atoms, monoglycerol ethers of saturated and/or unsaturated, branched and/or unbranched alcohols with a chain length of from about 8 to about 24, in particular from about 12 to about 18, carbon atoms, diglycerol ethers of saturated and/or unsaturated, branched and/or unbranched alcohols with a chain length of from about 8 to about 24, in particular of from about 12 to about 18, carbon atoms, propylene glycol esters of saturated and/or unsaturated, branched and/or unbranched alkanecarboxylic acids with a chain length of from about 8 to about 24, in particular from about 12 to about 18, carbon atoms, and sorbitan esters of saturated and/or unsaturated, branched and/or unbranched alkanecarboxylic acids with a chain length of from about 8 to about 24, in particular from about 12 to about 18, carbon atoms.

Examples of particularly advantageous W/O emulsifiers include glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol(2) stearyl ether (steareth-2), glyceryl monolaurate, glyceryl monocaprate, and glyceryl monocaprylate.

It is possible according to the invention to keep the total content of emulsifiers less to than about 20% by weight, based on the total weight of the (microemulsion) gel. It is preferred to keep the total content of emulsifiers between about 10% by weight and about 14% by weight, based on the total weight of the emulsion gel.

The oil phase of the emulsion gels according to the invention is advantageously selected from one or more of esters of saturated and/or unsaturated, branched and/or unbranched alkanecarboxylic acids with a chain length of from about 3 to about 30 carbon atoms and saturated and/or unsaturated, branched and/or unbranched alcohols with a chain length of from about 3 to about 30 carbon atoms, esters of aromatic carboxylic acids and saturated and/or unsaturated, branched and/or unbranched alcohols with a chain length of from about 3 to about 30 carbon atoms. Such ester oils may particularly advantageously be selected from one or more of dicaprylyl carbonate, octyldodecanol, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, and synthetic, semisynthetic and natural mixtures of such esters, e.g. jojoba oil.

In addition, the oil phase may advantageously be selected from one or more of branched and unbranched hydrocarbons and hydrocarbon waxes, silicone oils, dialkyl ethers, saturated or unsaturated, branched or unbranched alcohols, and the fatty acid triglycerides, namely the triglycerol esters of saturated and/or unsaturated, branched and/or unbranched alkanecarboxylic acids with a chain length of from about 8 to about 24, in particular from about 12 to about 18, carbon atoms. The fatty acid triglycerides may, for example, advantageously be selected from one or more of synthetic, semisynthetic and natural oils, e.g., one or more of olive oil, sunflower oil, soybean oil, groundnut oil, rapeseed oil, almond oil, palm oil, coconut oil, palm kernel oil and the like.

Any mixtures of such oil and wax components may also be used advantageously for the purposes of the present invention.

It may also in some cases be advantageous to use waxes, for example cetyl palmitate, as the sole lipid component of the oil phase. In such cases, the O/W microemulsion gels according to the invention may also in some cases be formed as microdispersions of solid wax particles.

The oil phase may advantageously comprise one or more of ethylhexyl palmitate, 2-ethylhexyl isostearate, octyldodecanol, isotridecyl isononanoate, isoeicosane, 2-ethylhexyl cocoate, $C_{12-15}$-alkyl benzoate, caprylic/capric triglyceride, dicaprylyl ether, dicaprylyl carbonate.

Particularly advantageous mixtures include those of ethylhexyl palmitate and dicaprylyl carbonate, of ethylhexyl palmitate and 2-ethylhexyl isostearate, of ethylhexyl palmitate and isotridecyl isononanoate, and of ethylhexyl palmitate, octyldodecanol, 2-ethylhexyl isostearate and isotridecyl isononanoate.

Paraffin oil, squalane and squalene are examples of hydrocarbons which may advantageously be used for the purposes of the present invention.

The oil phase may advantageously also have a content of cyclic or linear silicone oils, or consist entirely of such oils, although it is preferable to use an additional content of other oil phase components apart from the silicone oil(s).

Advantageously, cyclomethicone (decamethylcyclopentasiloxane) may be used as the silicone oil for use according to the present invention. However, other silicone oils may also be used advantageously for the purposes of the present invention, for example hexamethylcyclotrisiloxane, octamethylcyclotetrasiloxane, polydimethylsiloxane, and/or poly (methylphenylsiloxane).

Mixtures of cyclomethicone and isotridecyl isononanoate, of cyclomethicone and ethylhexyl palmitate, of cyclomethicone and 2-ethylhexyl isostearate, and of cyclomethicone and octyldodecanol may also be particularly advantageous.

The polyols, in particular the triols, which may act as crosslinking substances in the invention form an independent gel network and hold the network and the emulsion droplets together at the points of intersection of the network. The polyols may also contribute to the optical transparency of the emulsion gels.

The one or more polyols may advantageously be selected from one or more of short-chain, branched and/or unbranched diols, sorbitols and triols. Glycerol, propylene glycol, dipropylene glycol, sorbitol, and butylene glycol are examples of particularly advantageous polyols for use in the present invention.

Glycerol and mixtures of glycerol and propylene glycol, mixtures of glycerol and dipropylene glycol, mixtures of glycerol and sorbitol, mixtures of glycerol and butylene glycol may also be particularly advantageous.

The transparent gels according to the invention may advantageously be prepared by bringing a mixture of the basic components, comprising water phase, oil phase, one or more of the O/W emulsifiers according to the invention, optionally, one or more W/O emulsifiers, and if desired further auxiliaries, additives and/or active ingredients, to a temperature at which all of the components have substantially dissolved. Subsequently, the formed emulsion gel is cooled to room temperature. This preferably takes place with stirring.

Surprisingly, it is in each case possible to dispense with a homogenization step.

Advantageously, large amounts of acidic aluminium and/or aluminium/zirconium salts can be stably incorporated into the emulsions. From about 5% to about 40% by weight, in particular from about 7% to about 25% by weight, of aluminium chlorohydrate and/or aluminium/zirconium chlorohydrate may be stably incorporated into the emulsions. In this regard, the described concentration ranges refer to the so-called active contents of the antiperspirant complexes: in the case of the aluminium compounds they refer to anhydrous complexes, in the case of the aluminium/zirconium compounds they refer to anhydrous and buffer-free complexes. The buffer used here is usually glycine.

The following listing of antiperspirant agents which may be used advantageously in accordance with the present invention is not to be construed to be limiting in any way:

aluminium salts (of the empirical formula $[Al_2(OH)_mCl_n]$, where m+n=6):

Aluminium salts, such as aluminium chloride $AlCl_3$, aluminium sulphate $Al_2(SO_4)_3$ Aluminium chlorohydrate $[Al_2(OH)_5Cl]×H_2O$ Standard Al complexes: Locron L (Clariant), Chlorhydrol (Reheis), ACH-303 (Summit), Aloxicoll L (Giulini).

Activated Al complexes: Reach 501 (Reheis), AACH-324 (Summit)

Aluminium sesquichlorohydrate $[Al_2(OH)_{4.5}Cl_{1.5}] \times H_2O$

Standard Al complexes: aluminium sesquichlorohydrate (Reheis), ACH-308 (Summit), Aloxicoll 31 L (Giulini)

Activated Al complexes: Reach 301 (Reheis)

Aluminium dichlorohydrate $[Al_2(OH)_4Cl_2] \times H_2O$

Aluminium/zirconium salts:

Aluminium/zirconium trichlorohydrex glycine $[Al_4Zr(OH)_{13}Cl_3] \times H_2O \times Gly$ Standard Al/Zr complexes: Rezal 33GP (Reheis), AZG-7164 (Summit), Zirkonal P3G (Giulini)

Activated Al/Zr complexes: Reach AZZ 902 (Reheis), AAZG-7160 (Summit), Zirkonal AP3G (Giulini)

Aluminium/zirconium tetrachlorohydrex glycine $[Al_4Zr(OH)_{12}Cl_4] \times H_2O \times Gly$ Standard Al/Zr complexes: Rezal 36G (Reheis), AZG-368 (Summit), Zirkonal L435G (Giulini)

Activated Al/Zr complexes: Reach AZP 855 (Reheis), AAZG-6313-15 (Summit), Zirkonal AP4G (Giulini)

Aluminium/zirconium pentachlorohydrex glycine $[Al_8Zr(OH)_{23}Cl_5] \times H_2O \times Gly$ Standard Al/Zr complexes: Rezal 67 (Reheis), Zirkonal L540 (Giulini)

Activated Al/Zr complexes: Reach AZN 885 (Reheis)

Aluminium/zirconium octachlorohydrex glycine $[Al_8Zr(OH)_{20}Cl_8] \times H_2O \times Gly$ Glycine-free aluminium/zirconium salts may also be advantageous.

In this regard, the use of antiperspirant agents from the raw material classes of aluminium and aluminium/zirconium salts should not be limited to the standard commercial, mainly aqueous solutions, such as, for example, Locron L (Clariant), but it may also be advantageous to use the standard commercial anhydrous powders of the same raw materials by incorporation into the claimed formulations, such as, for example, Locron P (Clariant).

The use of so-called AT-salt suspensions in which aluminium and aluminium/zirconium salts present in powder form are supplied dispersed in various oils may also be advantageous.

Furthermore, it may be advantageous to use special aluminium and aluminium/zirconium salts which are supplied as glycol complexes for improving the solubility.

Further advantageous antiperspirant agents include those which are based, instead of on aluminium or zirconium, on other metals, such as, for example, beryllium, titanium and hafnium.

It is noted that the list of antiperspirant agents which may be used should not be construed to be limited to metal-containing raw materials. Rather, compounds which comprise non-metals such as, e.g., boron, and those which are classified as organic agents, such as, for example, anticholinergics, may also be advantageous. Advantageous in this sense are also polymers which may either contain metals or be metal-free.

The effect arising in numerous preparations of a visible white residue remaining on the skin following application of the preparation is usually perceived by the user as being undesirable. In anhydrous preparations, the use of propoxylated alcohols has proven useful for concealing this phenomenon. In the case of water-containing preparations, no satisfactory solution to this problem is hitherto known. The addition of propoxylated alcohols having from about 10 to about 20 propyloxy units and from about 2 to about 10 carbon atoms in the alkyl chain, in particular PPG-14 butyl ether, as component of the medium-polar oil phase overcomes the described shortcoming of the prior art reliably, concealing the appearance of such white residues.

Deodorants may advantageously be added to preparations according to the invention. Customary cosmetic deodorants are based on various activity principles.

The use of antimicrobial substances in cosmetic deodorants can reduce the bacterial flora on the skin. In this connection, in the ideal case, only the odor-causing microorganisms should be effectively reduced. The flow of sweat itself is not influenced by this, and in an ideal case only microbial decomposition of the sweat is temporarily stopped. The combination of adstringents with antimicrobially effective substances in one and the same composition is also customary.

All active ingredients customary for deodorants may be used advantageously in the present invention, for example, odor concealers such as the customary perfume constituents, odor absorbers, for example the sheet silicates described in DE 40 09 347, and of these, in particular, montmorillonite, kaolinite, illite, beidellite, nontronite, saponite, hectorite, bentonite, smectite, and also, for example, zinc salts of ricinoleic acid. Antimicrobial agents are likewise suitable for incorporation into the emulsions according to the invention. Advantageous substances are, for example, 2,4,4'-trichloro-2'-hydroxydiphenyl ether (Irgasan), 1,6-di(4-chlorophenylbiguanido)hexane (chlorhexidine), 3,4,4'-trichlorocarbanilide, quaternary ammonium compounds, oil of cloves, mint oil, thyme oil, triethyl citrate, farnesol (3,7,11-trimethyl-2,6,10-dodecatrien-1-ol), and the effective agents described in DE 37 40 186, DE 39 38 140, DE 42 04 321, DE 42 29 707, DE 42 29 737, DE 42 37 081, DE 43 09 372, DE 43 24 219. Sodium bicarbonate may also be used advantageously.

The above list of active ingredients or active ingredient combinations which can be used in the emulsions according to the invention is not intended to be limiting in any way.

The amount of deodorants (one or more substances) in the preparations of the present invention will usually be from about 0.01% to about 10% by weight, particularly preferably from about 0.05% to about 5% by weight, in particular from about 0.1% to about 1% by weight, based on the total weight of the preparation.

The cosmetic and dermatological preparations according to the invention can comprise cosmetic auxiliaries, as are customarily used in such preparations, e.g. preservatives, bactericides, perfumes, antifoams, dyes, pigments which have a colouring action, thickeners, moisturizing and/or humectant substances, fats, oils, waxes, antioxidants, vitamins and/or derivatives thereof, photoprotective filters or other customary constituents of a cosmetic or dermatological formulation such as, e.g., alcohols, polyols, polymers, foam stabilizers, organic solvents or silicone derivatives, and moisturizers.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description making apparent to those of skill in the art how the several forms of the present invention may be embodied in practice. Unless stated otherwise, all amounts, fractions and percentages are based on the weight and the total amount or on the total weight of the preparations.

Exemplary formulations for transparent antiperspirant gels

| INCI name(s) | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| Octyldodeceth-20 | | | | | | | | 13.00 | | |
| Octyldodeceth-25 | 13.00 | 13.00 | 12.00 | 13.00 | 13.00 | 13.00 | 12.00 | | | |
| Ceteareth-15 | | | | | | | | | 12.00 | 13.00 |
| Cyclomethicone | | 40.00 | 15.00 | | | | | | 15.00 | |
| Dicaprylyl Carbonate | | | | | | | 35.00 | | | |
| Ethylhexyl Palmitate | 40.00 | | | 40.00 | 40.00 | 40.00 | | 40.00 | | 40.00 |
| Octyldodecanol | | | 15.00 | | | | | | 15.00 | |
| Glycerol | 15.00 | 15.00 | 15.00 | 13.00 | 13.00 | | | 15.00 | 15.00 | 15.00 |
| Butylene Glycol | | | | | | 13.00 | 15.00 | | | |
| Aluminium Chlorohydrate (50% solution) | 20.00 | 20.00 | 20.00 | 20.00 | 15.00 | 20.00 | 20.00 | 20.00 | 30.00 | 20.00 |
| Water | 12.00 | 12.00 | 23.00 | 14.00 | 19.00 | 14.00 | 18.00 | 12.00 | 13.00 | 12.00 |
| Totals: | 100.00 | 100.00 | 100.00 | 100.00 | 100.00 | 100.00 | 100.00 | 100.00 | 100.00 | 100.00 |

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A cosmetic or dermatological composition for preventing excessive odor and sweat secretion by skin, comprising an optically translucent to transparent, substantially alcohol-free oil-in-water (O/W) type emulsion gel which comprises, based a total weight of the emulsion, (a) not more than about 20% by weight of one or more O/W emulsifiers selected from polyethoxylated O/W emulsifiers, polypropoxylated O/W emulsifiers and combinations thereof and of one or more optional W/O emulsifiers, (b) from about 1% to about 30% by weight of one or more polyols, and (c) from about 5% to about 40% by weight of one or more antiperspirants.

2. The composition of claim 1, wherein the composition is obtainable by mixing and heating components thereof until they have substantially dissolved, and then cooling to room temperature with stirring.

3. The composition of claim 1, wherein the emulsion comprises a microemulsion.

4. The composition of claim 1, wherein the emulsion comprises a discontinuous phase which comprises droplets which are joined together by the one or more polyols.

5. The composition of claim 4, wherein the droplets have an average size of less than about 100 nm.

6. The composition of claim 1, wherein the composition has a viscosity of from about 5,000 to about 500,000 mPa s.

7. The composition of claim 6, wherein the composition has a viscosity of up to about 400,000 mPa s.

8. The composition of claim 7, wherein the composition has a viscosity of at least about 10,000 mPa s.

9. The composition of claim 8, wherein the composition has a viscosity of up to about 300,000 mPa s.

10. The composition of claim 1, wherein the one or more antiperspirants comprise at least one acidic salt.

11. The composition of claim 10, wherein the acidic salt comprises at least one of aluminum and zirconium.

12. The composition of claim 11, wherein the one or more antiperspirants comprise at least one of an aluminum salt and an aluminum/zirconium salt in a total amount of at least about 5% by weight, based on a total weight of the composition.

13. The composition of claim 1, wherein the composition comprises from about 10% to about 30% by weight of the one or more antiperspirants, based on a total weight of the composition.

14. The composition of claim 1, wherein the composition comprises from about 0.1% to about 20% by weight of the one or more polyethoxylated O/W emulsifiers, based on a total weight of the composition.

15. The composition of claim 14, wherein the composition comprises from about 0.5% to about 18% by weight of the one or more polyethoxylated O/W emulsifiers.

16. The composition of claim 15, wherein the composition comprises from about 1% to about 14% by weight of the one or more polyethoxylated O/W emulsifiers.

17. The composition of claim 1, wherein the composition comprises from about 0.1% to about 20% by weight of the one or more polypropoxylated O/W emulsifiers, based on a total weight of the composition.

18. The composition of claim 17, wherein the composition comprises from about 0.5% to about 18% by weight of the one or more polypropoxylated O/W emulsifiers.

19. The composition of claim 18, wherein the composition comprises from about 1% to about 14% by weight of the one or more polypropoxylated O/W emulsifiers.

20. The composition of claim 1, wherein the composition comprises from about 0.1% to about 5% by weight of the one or more W/O emulsifiers, based on a total weight of the composition.

21. The composition of claim 20, wherein the composition comprises from about 0.5% to about 3.5% by weight of the one or more W/O emulsifiers.

22. The composition of claim 21, wherein the composition comprises from about 1% to about 2.5% by weight of the one or more W/O emulsifiers.

23. The composition of claim 1, wherein the composition comprises from about 5% to about 25% by weight of the one or more polyols, based on a total weight of the composition.

24. The composition of claim 23, wherein the composition comprises from about 8% to about 20% by weight of the one or more polyols.

25. The composition of claim 1, wherein the one or more polyols comprise at least one of glycerol, propylene glycol, dipropylene glycol, sorbitol, and butylene glycol.

26. The composition of claim 25, wherein the one or more polyols comprise glycerol.

27. The composition of claim 26, wherein the one or more polyols comprise glycerol and at least one of propylene glycol, dipropylene glycol, sorbitol, and butylene glycol.

28. The composition of claim 1, wherein the composition comprises, based on a total weight of the composition, at least one of from about 1% to about 14% by weight of the one or more polyethoxylated O/W emulsifiers and from about 1% to about 14% by weight of the one or more polypropoxylated O/W emulsifiers, and from about 8% to about 20% by weight of the one or more polyols.

29. The composition of claim 28, wherein the composition further comprises from about 1% to about 2.5% by weight of the one or more W/O emulsifiers.

30. The composition of claim 28, wherein the one or more polyols comprise glycerol.

31. The composition of claim 30, wherein the composition comprises from about 10% to about 30% by weight of the one or more antiperspirants, based on the total weight of the composition.

32. The composition of claim 31, wherein the one or more antiperspirants comprise at least one of an acidic aluminum salt and an acidic aluminum/zirconium salt in a total amount of at least about 5% by weight, based on the total weight of the composition.

33. The composition of claim 32, wherein the composition has a viscosity of from about 10,000 to about 300,000 mPa s.

34. The composition of claim 1, wherein the composition further comprises an active ingredient.

35. The composition of claim 1, wherein the composition further comprises at least one of a perfume and a fragrance.

36. The composition of claim 33, wherein the composition comprises a microemulsion.

37. The composition of claim 28, wherein the composition comprises droplets of a discontinuous phase which are linked by the one or more polyols.

38. The composition of claim 37, wherein the droplets have an average size of less than about 100 nm.

39. A process for making the composition of claim 1, wherein the process comprises heating a mixture of components thereof until the components have substantially dissolved and thereafter cooling the mixture to room temperature with stirring.

40. The process of claim 39, wherein the process does not include a homogenization operation.

41. The composition of claim 1, wherein the composition is a thick liquid or a semi-solid.

42. A cosmetic stick which comprises the composition of claim 1.

43. A deodorant roll-on container which comprises the composition of claim 1.

44. An atomizer pump container which comprises the composition of claim 1.

45. A method of reducing the secretion of sweat by skin, wherein the method comprises applying to at least parts of the skin the composition of claim 1.

46. A method of reducing excessive odor generated by skin, wherein the method comprises applying to at least parts of the skin the composition of claim 1.

47. The method of claim 45, wherein the composition is applied in an armpit area.

48. The method of claim 45, wherein the composition is applied in a genital area.

* * * * *